US 7,752,682 B2

(12) United States Patent
VanDerWoude et al.

(10) Patent No.: US 7,752,682 B2
(45) Date of Patent: Jul. 13, 2010

(54) PERSONAL PROTECTION SYSTEM INCLUDING A HELMET AND A HOOD, THE HELMET INCLUDING A VENTILATION SYSTEM THAT BLOWS AIR ON THE NECK OF THE WEARER

(75) Inventors: Brian J. VanDerWoude, Portage, MI (US); Bruce D. Henniges, Galesburg, MI (US); Richard F. Huyser, Kalamazoo, MI (US); Marshall K. Proulx, Kalamazoo, MI (US)

(73) Assignee: Stryker Corporation, Kalamazoo, MI (US)

( * ) Notice: Subject to any disclaimer, the term of this patent is extended or adjusted under 35 U.S.C. 154(b) by 1090 days.

(21) Appl. No.: 11/277,424

(22) Filed: Mar. 24, 2006

(65) Prior Publication Data

US 2006/0213523 A1    Sep. 28, 2006

Related U.S. Application Data

(60) Provisional application No. 60/664,900, filed on Mar. 24, 2005.

(51) Int. Cl.
*A42B 1/06* (2006.01)
*A42B 1/24* (2006.01)
*A42C 5/04* (2006.01)

(52) U.S. Cl. .................... 2/410; 2/422; 2/171.3
(58) Field of Classification Search ............ 2/410, 2/7, 8.1, 8.2, 424, 171.3; 128/863, 201.22; 607/96, 104, 108, 109, 110, 112

See application file for complete search history.

(56) References Cited

U.S. PATENT DOCUMENTS 1,037,206 A    9/1912   Clifford 1,766,272 A    6/1930   Vallier (Continued)

FOREIGN PATENT DOCUMENTS

GB    2183488    6/1987

(Continued)

OTHER PUBLICATIONS

International Application No. PCT/US2006/010654; International filing date Mar. 24, 2006; International Search Report dated Aug. 3, 2006; International Search Report and Written Opinion mailing date Nov. 22, 2006.

*Primary Examiner*—Gary L Welch
*Assistant Examiner*—Amber R Anderson
(74) *Attorney, Agent, or Firm*—Howard & Howard Attorneys PLLC

(57) ABSTRACT

A personal protection system is mountable to a user for distributing air to the user includes a shell providing structure. A fan module is supported by the shell for generating a flow of air. Cushioning is provided between the fan module and the shell to reduce vibrations and noise. The fan module includes a fan with blades having an airfoil shape for added noise reduction. An air flow channel is in fluid communication with the fan module for routing the flow of air. A pair of nozzle tips are in fluid communication with the air flow channel and are rotatably adjustable to allow directional adjustment of the flow of air toward a neck of the user. The personal protection system also includes a face shield with multiple removable layers which are sterilized as a unit using gamma radiation.

20 Claims, 11 Drawing Sheets

U.S. PATENT DOCUMENTS

| | | | |
|---|---|---|---|
| 2,579,942 A * | 12/1951 | MacLean | 128/201.25 |
| 2,739,310 A | 3/1956 | Frieder et al. | |
| 3,018,776 A | 1/1962 | Saitta et al. | |
| 3,025,525 A | 3/1962 | Larson | |
| 3,048,776 A | 8/1962 | Logan | |
| 3,058,463 A | 10/1962 | Goodrich, Jr. | |
| 3,214,809 A | 11/1965 | Edwards | |
| 3,529,594 A | 9/1970 | Charnley | |
| 3,803,640 A | 4/1974 | Ericson | |
| 3,822,698 A | 7/1974 | Guy | |
| 3,881,198 A | 5/1975 | Waters | |
| 3,950,112 A | 4/1976 | Crump | |
| 3,955,570 A | 5/1976 | Hutter | |
| 3,963,021 A * | 6/1976 | Bancroft | 128/201.25 |
| 4,019,508 A | 4/1977 | Der Estephanian | |
| 4,038,979 A | 8/1977 | McCosker | |
| 4,055,123 A | 10/1977 | Heidelberg | |
| 4,133,308 A | 1/1979 | Lowe | |
| 4,136,688 A | 1/1979 | Gorman | |
| 4,227,520 A * | 10/1980 | Lord | 128/201.24 |
| 4,280,491 A | 7/1981 | Berg et al. | |
| 4,296,746 A | 10/1981 | Mason, Jr. | |
| 4,320,256 A | 3/1982 | Freeman | |
| 4,336,799 A | 6/1982 | Almasi | |
| 4,469,097 A | 9/1984 | Kelman | |
| 4,549,541 A | 10/1985 | Sundahl | |
| 4,589,408 A | 5/1986 | Singer | |
| 4,590,951 A | 5/1986 | O'Connor | |
| 4,619,254 A | 10/1986 | Moretti | |
| 4,651,727 A | 3/1987 | Howorth | |
| 4,667,667 A | 5/1987 | Schnoor | |
| 4,672,968 A | 6/1987 | Lenox | |
| 4,674,492 A | 6/1987 | Niemeyer | |
| 4,676,236 A | 6/1987 | Piorkowski | |
| 4,711,033 A | 12/1987 | Mitchell | |
| 4,711,539 A | 12/1987 | Krusas et al. | |
| 4,730,612 A | 3/1988 | Dampney | |
| 4,864,654 A | 9/1989 | Schriver | |
| 4,875,477 A | 10/1989 | Waschkle | |
| 4,888,831 A | 12/1989 | Oleson | |
| 4,901,716 A | 2/1990 | Stackhouse | |
| 4,951,662 A | 8/1990 | Townsend | |
| 5,003,973 A | 4/1991 | Ford | |
| 5,009,225 A | 4/1991 | Vrabel | |
| 5,042,474 A | 8/1991 | Williamson | |
| 5,048,516 A | 9/1991 | Soderberg | |
| 5,054,479 A | 10/1991 | Yelland | |
| 5,054,480 A | 10/1991 | Bare | |
| 5,069,205 A | 12/1991 | Urso | |
| 5,088,117 A | 2/1992 | Fulmer | |
| 5,104,430 A | 4/1992 | Her-Mous | |
| 5,125,402 A | 6/1992 | Greenough | |
| 5,142,704 A | 9/1992 | Viemeister | |
| 5,142,706 A | 9/1992 | Layhon | |
| 5,237,707 A | 8/1993 | Lowrie | |
| 5,253,642 A | 10/1993 | Stackhouse | |
| 5,283,914 A | 2/1994 | James | |
| 5,342,121 A | 8/1994 | Koria | |
| 5,349,949 A | 9/1994 | Schegerin | |
| 5,373,588 A | 12/1994 | Hede | |
| 5,410,757 A | 5/1995 | Vienamo | |
| 5,452,712 A | 9/1995 | Richardson | |
| 5,492,116 A | 2/1996 | Scarberry | |
| 5,503,146 A | 4/1996 | Froehlich | |
| 5,515,843 A | 5/1996 | Chang | |
| 5,525,278 A | 6/1996 | Krosch | |
| 5,533,500 A | 7/1996 | Her-Mou | |
| 5,549,104 A | 8/1996 | Crump | |
| 5,553,500 A | 9/1996 | Grahn | |
| 5,564,124 A | 10/1996 | Elsherif | |
| 5,577,495 A | 11/1996 | Murphy | |
| 5,588,153 A | 12/1996 | Ignon | |
| 5,592,936 A | 1/1997 | Thomas | |
| 5,601,078 A | 2/1997 | Schaller | |
| 5,655,374 A | 8/1997 | Santilli | |
| 5,664,566 A | 9/1997 | McDonald | |
| 5,669,375 A | 9/1997 | Dahrendorf | |
| 5,682,618 A | 11/1997 | Johnson | |
| 5,687,713 A | 11/1997 | Bahr | |
| 5,690,095 A | 11/1997 | Glynn | |
| 5,711,033 A | 1/1998 | Green | |
| 5,720,281 A | 2/1998 | Allen | |
| 5,879,493 A | 3/1999 | Johnson | |
| 5,887,281 A | 3/1999 | Green | |
| 6,014,971 A | 1/2000 | Danisch | |
| 6,189,327 B1 | 2/2001 | Strauss et al. | |
| 6,370,695 B2 * | 4/2002 | Paris et al. | 2/171.3 |
| 6,374,823 B1 | 4/2002 | Hajianpour | |
| 6,393,617 B1 | 5/2002 | Paris et al. | |
| 6,481,019 B2 | 11/2002 | Diaz et al. | |
| 6,622,311 B2 * | 9/2003 | Diaz et al. | 2/171.3 |
| 6,973,677 B2 | 12/2005 | Diaz et al. | |
| 6,990,691 B2 | 1/2006 | Klotz et al. | |
| 2001/0032348 A1 | 10/2001 | Diaz et al. | |
| 2004/0168459 A1 | 9/2004 | Blackstone | |
| 2005/0010992 A1 | 1/2005 | Klotz et al. | |

FOREIGN PATENT DOCUMENTS

| | | |
|---|---|---|
| WO | WO 88/09193 | 12/1988 |
| WO | WO 91/18569 | 12/1991 |

\* cited by examiner

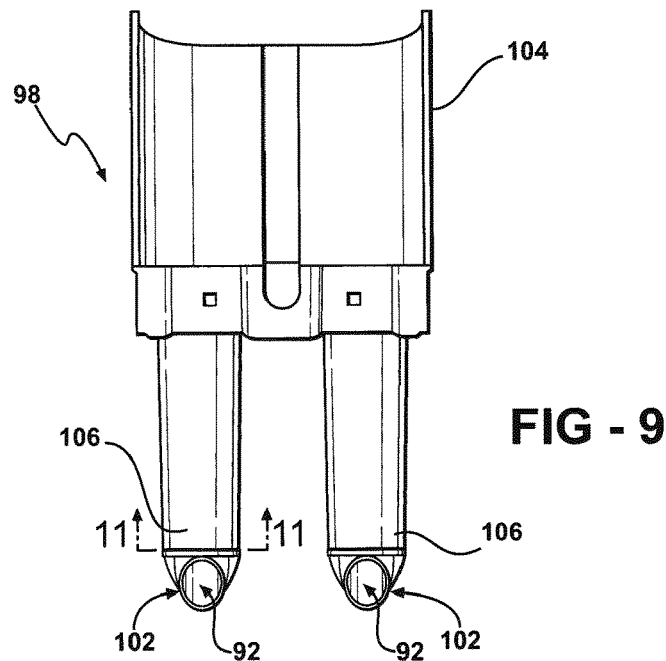
FIG - 9
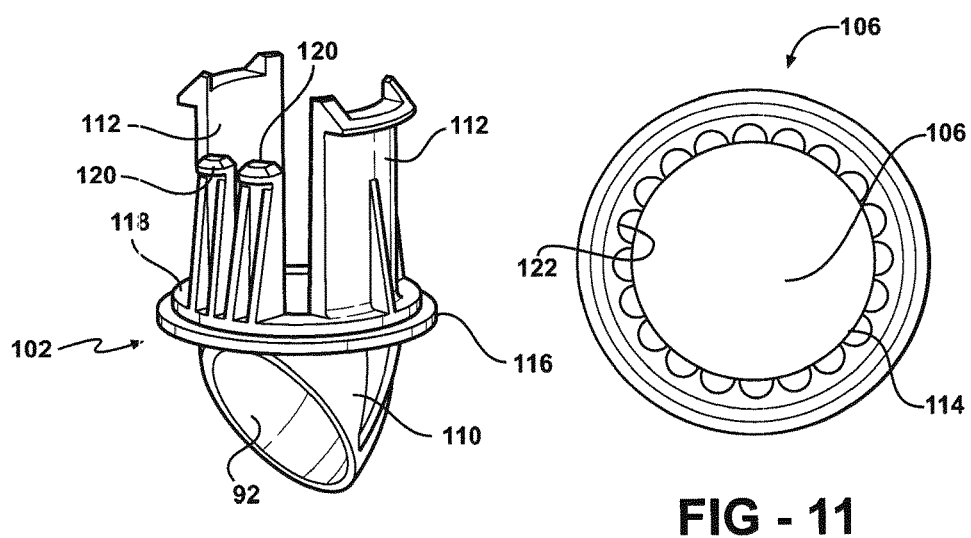
FIG - 10
FIG - 11

PERSONAL PROTECTION SYSTEM INCLUDING A HELMET AND A HOOD, THE HELMET INCLUDING A VENTILATION SYSTEM THAT BLOWS AIR ON THE NECK OF THE WEARER

CROSS REFERENCE TO RELATED APPLICATION

This application claims the benefit of provisional application Ser. No. 60/664,900 filed Mar. 24, 2005, which is hereby incorporated by reference.

BACKGROUND OF THE INVENTION

1. Field of the Invention

The subject invention generally relates to a personal protection system mountable to a user for distributing air to the user. The personal protection system is utilized in the medical profession during surgical procedures. The subject invention more specifically relates to a helmet assembly and gown for use in the personal protection system.

2. Description of the Prior Art

Personal protection systems and helmet assemblies utilized in personal protection systems are known in the art. As indicated above, personal protection systems and helmet assemblies are worn by users throughout the medical profession, such as surgeons, during surgical procedures.

Conventional personal protection systems and helmet assemblies are deficient for one reason or another. For example, U.S. Pat. No. 6,990,691 to Klotz et al. (the '691 patent) discloses a helmet assembly that draws air in with a fan assembly and distributes the air to front and rear air exits. However, when the helmet assembly is worn by the user, the air exit is disposed such that the air is vented near the middle of the back of the head of the user. Thus, the air cannot be directed toward the neck of the user, where most surgeons desire the air's cooling presence.

Other deficiencies of prior art personal protection systems are with the fan assembly. For instance, the shape of the blades of the fan, which rotate to draw in air, do not provide for the most efficient and quietest flow of air possible. This causes excessive power consumption, which leads to premature drain of battery packs, and excessive noise, which can be distracting for a surgeon performing delicate operations.

Furthermore, the prior art helmet assemblies tend to transfer vibrations caused by the rotation of the fan to the user, as well as being noisy in general. The vibrations, as well as the noise, can be distracting to the surgeon, who obviously needs to focus his efforts at the complex task at hand.

Yet another deficiency of the '691 patent concerns the multiple removable layers disposed on the face shield. The '691 patent is silent as to sterility of the multiple removable layers. However, sterilization concerns are of an utmost importance for any product involved in the surgical process.

For the above mentioned reasons, it is desirous to provide a personal protection system which provides more control over air flow to the neck of the user and which provides more efficient and quieter means for moving the flow of air. Furthermore, it is desirous to provide a personal protection system which noise and vibrations, which can be distracting to the surgeon, are kept to a minimum. Moreover, it is desirous to provide a face shield with removable layers that is sterilized in an efficient manner.

SUMMARY OF THE INVENTION AND ADVANTAGES

In a first aspect of the invention, a personal protection unit is disclosed. The personal protection unit includes a support structure for suspending a hood over the head of an individual. A fan module is attached to the support structure, with the fan module receiving air and discharging air. A duct is connected to the support structure and has an opening positioned to receive the air discharged from the fan module. The duct is shaped to have a rear air exit. The duct is arranged relative to the fan module so that only a fraction of the air discharged from the fan module enters the duct. The duct extends from the support structure and the rear air exit is positioned so that air is discharged from the rear air exit directly onto the neck of the individual. By the duct extending from the support structure and discharging air directly on to the neck, the comfort of the individual (e.g., a surgeon) is increased, allowing the individual to focus on the task he or she is performing (e.g., surgery).

In a second aspect of the invention, the personal protection unit includes the support structure for suspending the hood over the head of the individual. The personal protection unit includes a fan for circulating air. A motor is attached to the support structure and is connected to the fan for actuating the fan. An elastomeric, vibration dampening member holds the motor to the support structure. The vibration dampening member helps to reduce transmission of noise and/or vibrations generated by the fan and/or motor to the user. Reduction of noise and/or vibrations will decrease distractions to the individual.

A third aspect of the subject invention provides the personal protection system with the hood formed of flexible sterilizable material, a portion of which is filter material, and shaped to be worn over the head. A transparent face shield is attached to the hood. The personal protection system includes a support structure for suspending the hood over the head. A fan is attached to the support structure for circulating air through the hood. A plurality of individually removable layers of sterile transparent material are disposed over the face shield.

A fourth aspect of the invention provides a method of assembling a sterilized hood assembly having a transparent face shield. The method includes the step of providing a hood formed from sterilizable flexible material, a portion of the material being filter material. A transparent face shield assembly is attached to the hood where the shield assembly includes a face shield. The method further includes the step of sterilizing the hood and face shield assembly using a sterilization process that does not adversely affect the filter material. The transparent shield assembly further includes a plurality of removable transparent layers disposed over the face shield. Sterilizing the face shield and removable layers together as a whole provides for a more effective assembly process by negating the possibility of introducing contaminants during subsequent assembly operations.

BRIEF DESCRIPTION OF THE DRAWINGS

Other advantages of the present invention will be readily appreciated, as the same becomes better understood by reference to the following detailed description when considered in connection with the accompanying drawings wherein:

FIG. 9 is a elevational view of a nozzle assembly of the present invention;

FIG. 10 is a perspective view of a nozzle tip of the nozzle assembly;

FIG. 11 is a bottom view showing a port of a nozzle of the nozzle assembly;

DETAILED DESCRIPTION OF THE INVENTION

Referring to the Figures, wherein like numerals indicate corresponding parts throughout the several views, a personal protection system or personal protection unit is generally shown at 20. The personal protection system 20 is mountable to a user (i.e., an individual) for distributing air to the user. The personal protection system 20 of the present invention is adapted from the personal protection systems disclosed in U.S. Pat. No. 6,481,019 to Diaz et al. (the '019 patent) and U.S. Pat. No. 6,973,677 to Diaz et al. (the '677 patent), which are hereby incorporated by reference.

Figure 1:
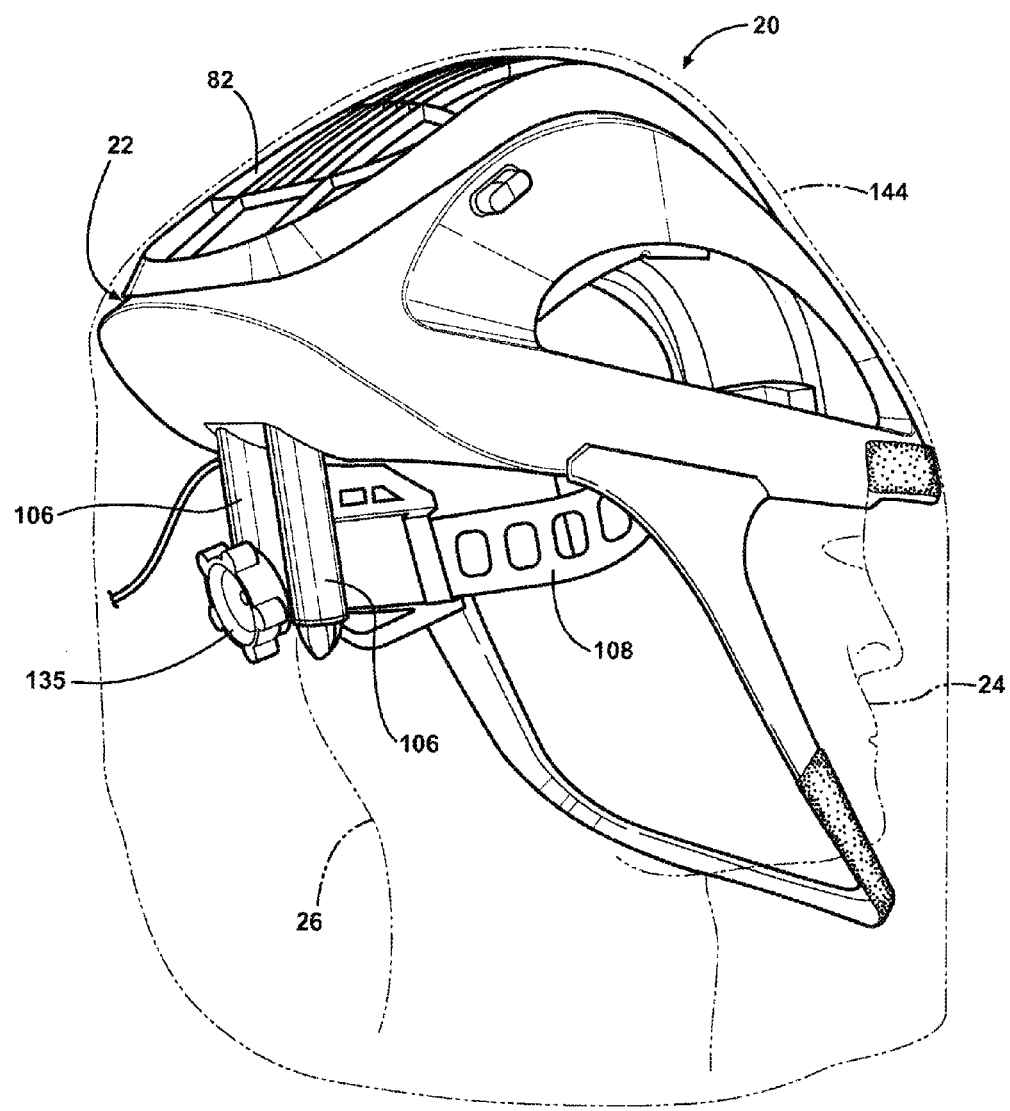
FIG. 1 is a perspective view of a personal protection system embodied as a helmet assembly mounted on a head of a user.

In the preferred embodiment, as shown in FIG. 1, the personal protection system 20 is implemented as a helmet 22 or helmet assembly 22. The personal protection system 20 filters air between a head 24 and body 26 of a user, e.g., a medical professional, and an environment external to the user. When in use, the preferred helmet assembly 22 of the personal protection system 20 is mounted to the head 24 of the user. The helmet assembly 22 distributes air about the head 24 of the user as will be described below. More specifically, in the preferred embodiment, the helmet assembly 22 distributes air toward both a front of the head 24, i.e., a face of the user, and towards the back of the head 24 and, more particularly, towards the back of the neck of the user.

The personal protection system 20 of the subject invention may be described hereafter in terms of the helmet assembly 22 of the preferred embodiment. However, this should not be construed as limiting the personal protection system 20 to the helmet assembly embodiment.

Figure 2:
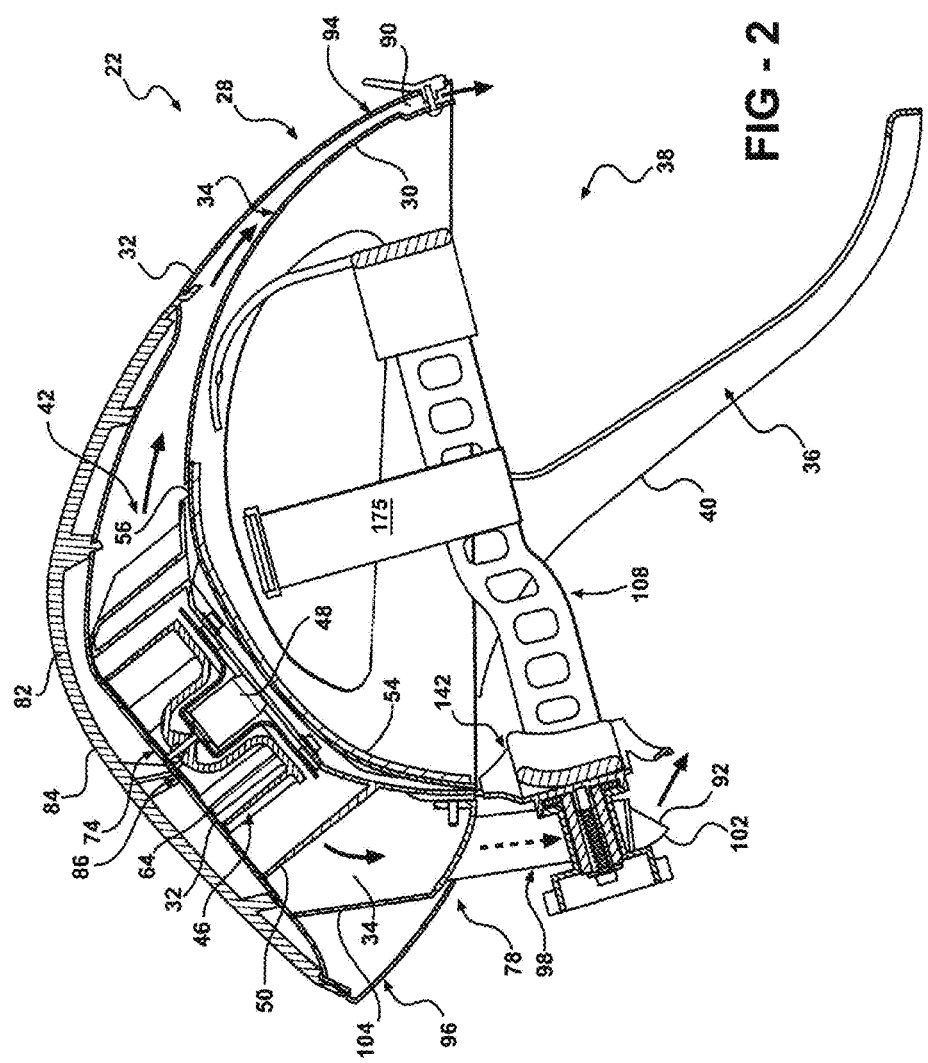
FIG. 2 is a cross-sectional view of the helmet assembly.

Referring to FIG. 2, the helmet assembly 22 includes a shell 28 providing structural support (i.e., a support structure 28). The shell 28 preferably includes an inner shell portion 30 facing the user and an outer shell portion 32 facing away from the user. In the preferred embodiment, the outer shell portion 32 is spaced apart from the inner shell portion 30 to define at least one air flow channel 34 between the inner and outer shell portions 30, 32. It is to be understood that the present invention may include more than one discrete air flow channel 34. However, the preferred embodiment includes a single unitary air flow channel 34 and the present invention will be described below in terms of this air flow channel 34. The shell 28 is preferably formed of acrylonitrile butadiene styrene (ABS), but may be formed, in alternative embodiments, of glass-filled polypropylene or other suitable materials.

The air flow channel 34 channels air about the head 24 of the user. The inner and outer shell portions 30, 32 may form the air flow channel 34 from a two-sheet thermoforming process which improves the structural strength of the shell 28. More specifically, each of the inner and outer shell portions 30, 32 include an outer periphery, and in the two-sheet thermoforming process, the inner and outer shell portions 30, 32 are pinched together at their outer peripheries. The air flow channel 34 is subsequently thermoformed between the pinched outer peripheries.

The helmet assembly 22 also includes a facial section 36 extending from the shell 28 to define a facial opening 38. The facial section 36 of the helmet assembly 22 is a chin bar 40. Preferably, the chin bar 40 is flexible and is formed of plastic. The chin bar 40 may also be formed of a polypropylene component. The flexibility of the chin bar 40 protects the user's face and also absorbs impact when the user contacts an external object with the helmet assembly 22.

Figure 3:
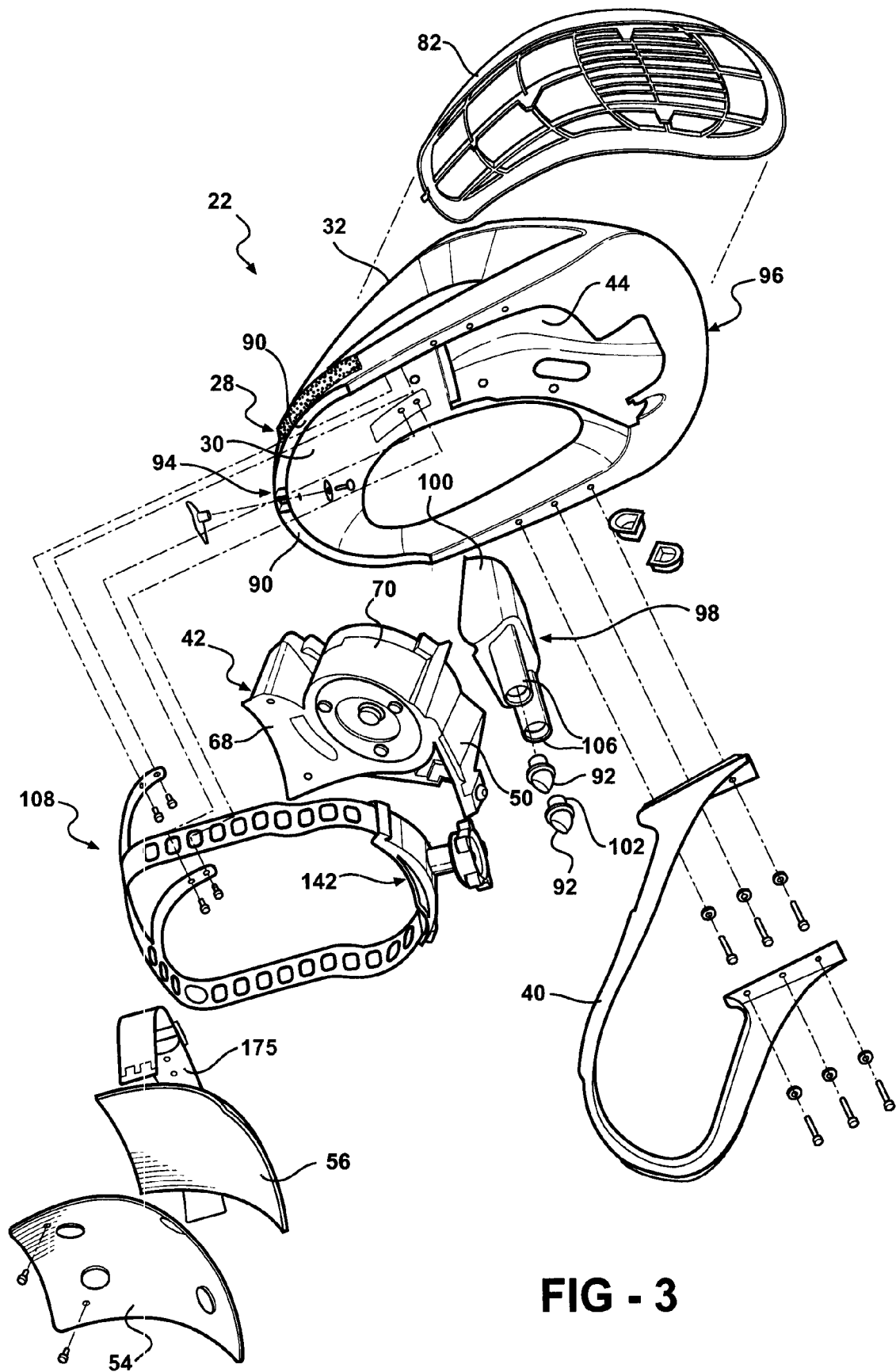
FIG. 3 is an exploded perspective view of the helmet assembly.
Figure 4:
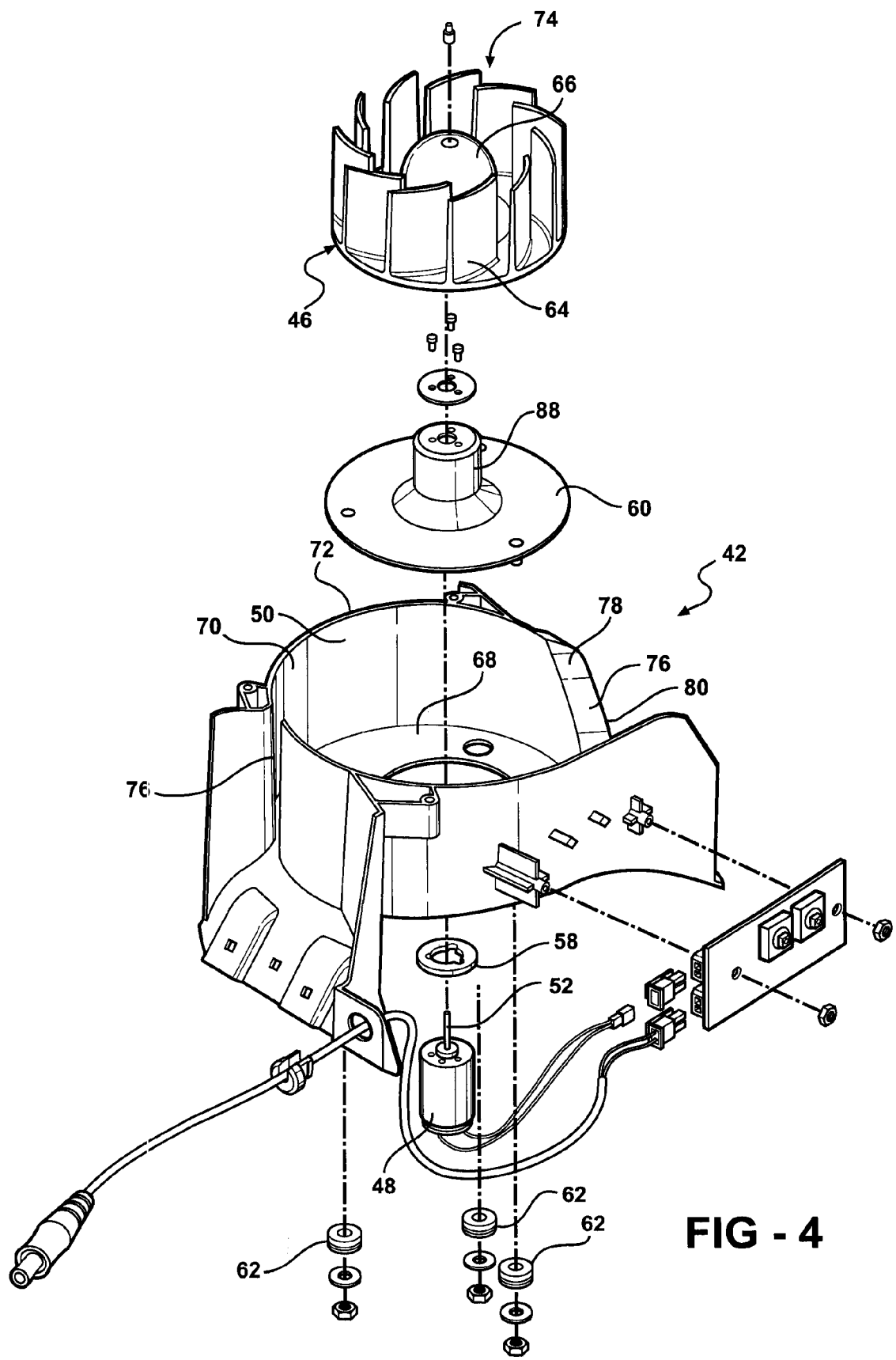
FIG. 4 is an exploded view of a preferred embodiment of a fan module of the present invention.

Referring now to FIG. 3, the helmet assembly 22 includes a fan module 42 disposed in and supported by the shell 28. More specifically, the fan module 42 is mounted in a cavity 44 formed by the shell 28. The fan module 42 operates to generate a flow of air which is fluidly communicated into the air flow channel 34. As shown in FIG. 4, the fan module 42 includes a fan 46 and a motor 48 mounted to a scroll housing 50. The motor 48 includes a drive shaft 52 operatively connected to the fan 46 to drive the fan 46 at a plurality of rotational speeds correlating to an amount, or a volume, of air flowing into the air flow channel 34. As appreciated by those skilled in the art, the rotational speeds of the fan 46 can be measured in revolutions per minute (RPMs).

Referring again to FIG. 3, a cover plate 54 is fixed to the shell 28 and the fan module 42 to hold in the fan module 42 in the cavity 44. A fan module cushion 56 is disposed between the cover plate 54 and a base of the fan module 42. The fan module cushion 56 reduces the transmission of noise from the motor 48 to the user.

Figure 5:
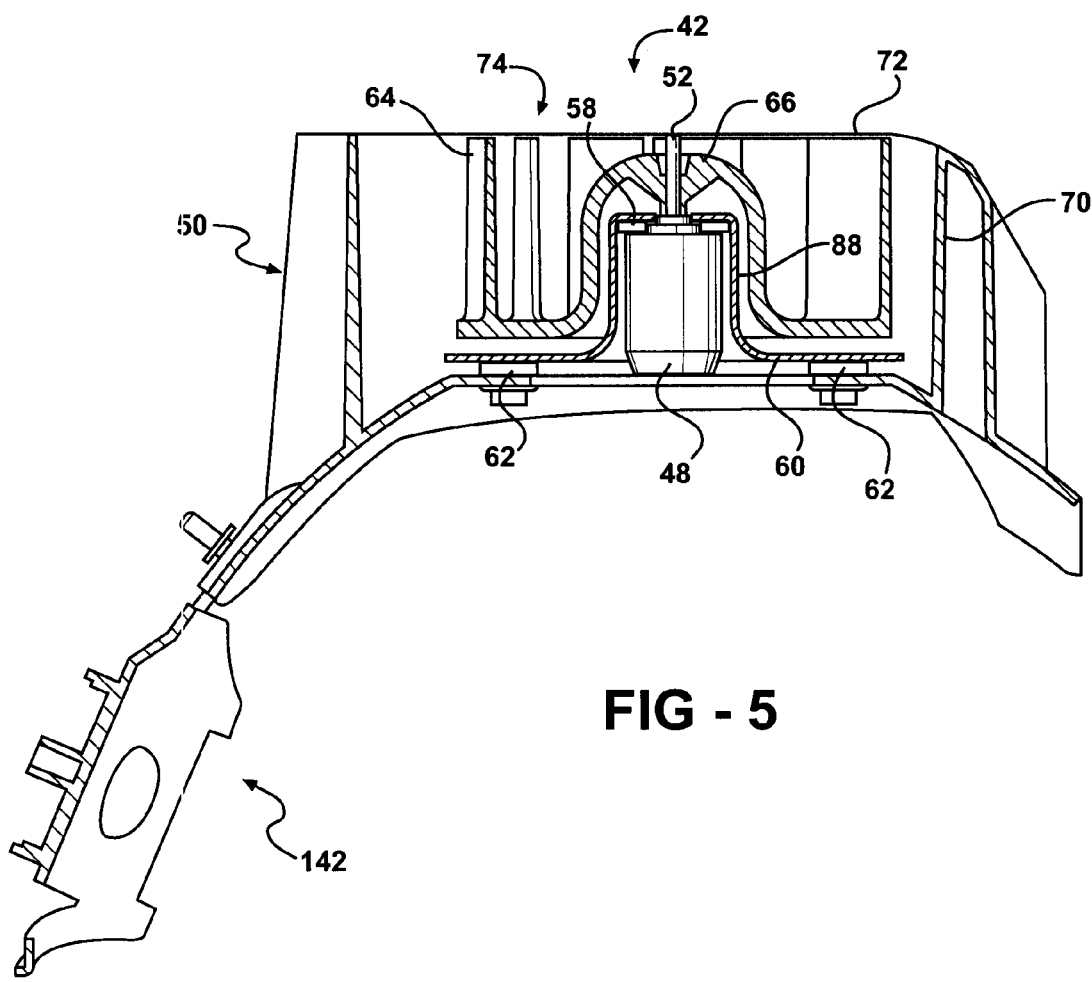
FIG. 5 is a cross-sectional view of the preferred embodiment of the fan module.

Referring to FIGS. 4 and 5, in the preferred embodiment, a motor cushion 58 is disposed between the motor 48 and a motor mount 60. A plurality of motor mount cushions 62, embodied as grommets, is placed between the motor mount 60 and the scroll housing 50 (although shown below the scroll housing 50 for clarity, the arrangement is best shown in FIG. 5). The motor cushion 58 and motor mount cushions 62 work together as a vibration dampening member to reduce shock loads and vibrations. More specifically, the motor mount cushions 62 are the primary component for shock reduction between the helmet structure, e.g., shell 28, and the motor 48, thereby extending the bearing life of the motor 48 and providing low sound characteristics. The motor mount cushions 62 completely isolate the motor 48 from the rest of the helmet structure. By having two sets of cushioning, i.e., the motor cushion 58 between the motor 48 and motor mount 60 and the motor mount cushions 62 between the motor mount 60 and the scroll housing 50, the transmission of energy between the helmet structure and the motor 48 can be fine tuned. The motor cushion 58 and the motor mount cushions 62 may be formed of foam and/or an elastomeric material.

Figure 6:
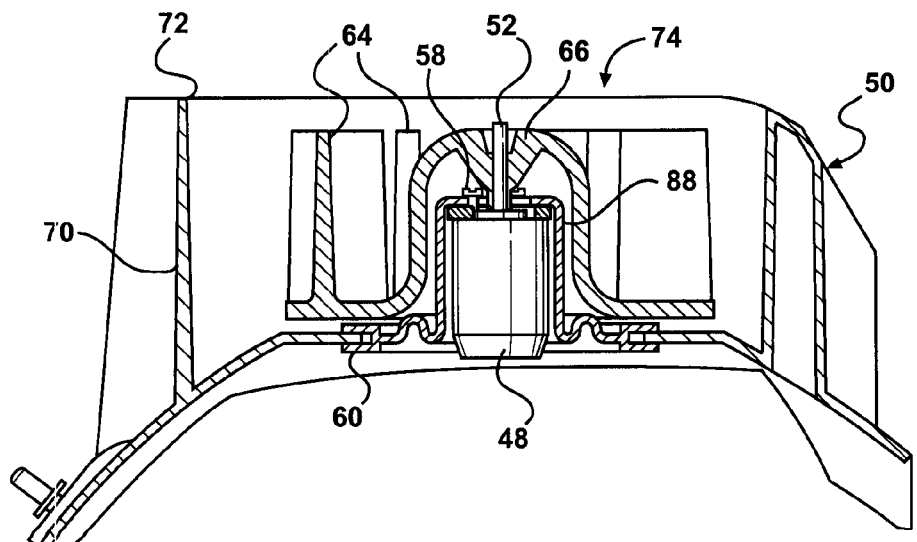
FIG. 6 is a cross-sectional view of an alternative embodiment of the fan module.

Referring to FIG. 6, in an alternative embodiment of the invention, the motor mount 60 for mounting the motor 48 to the scroll housing 50 is formed of elastomeric material. Preferably, the motor mount 60 is formed of silicone having a durometer of from 10 to 80 shore A. Much like the motor mount cushions 62 of the preferred embodiment, the elastomeric motor mount 60 reduces shock loads and vibrations. Moreover, the scroll housing 50 may be formed of glass-filled polypropylene to further reduce vibrations.

Figure 7:
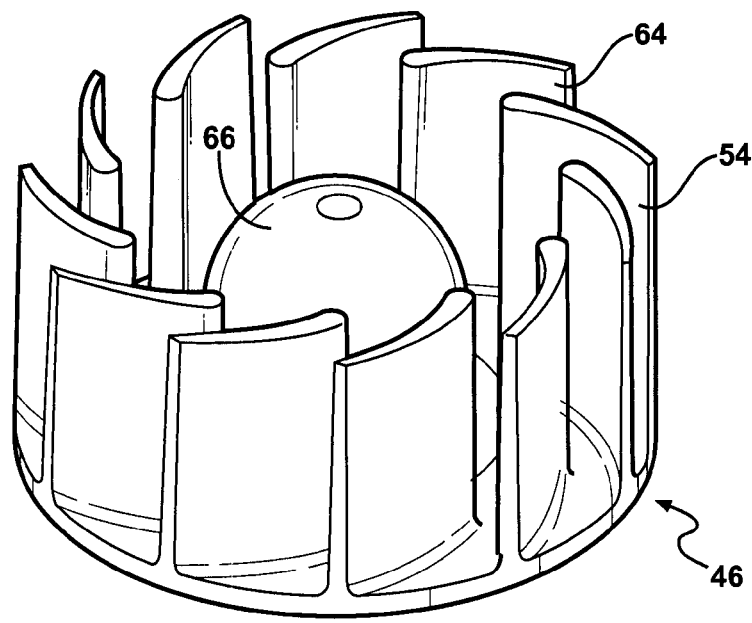
FIG. 7 is a perspective view of a fan of the fan module showing fan blades having an airfoil shape.
Figure 8:
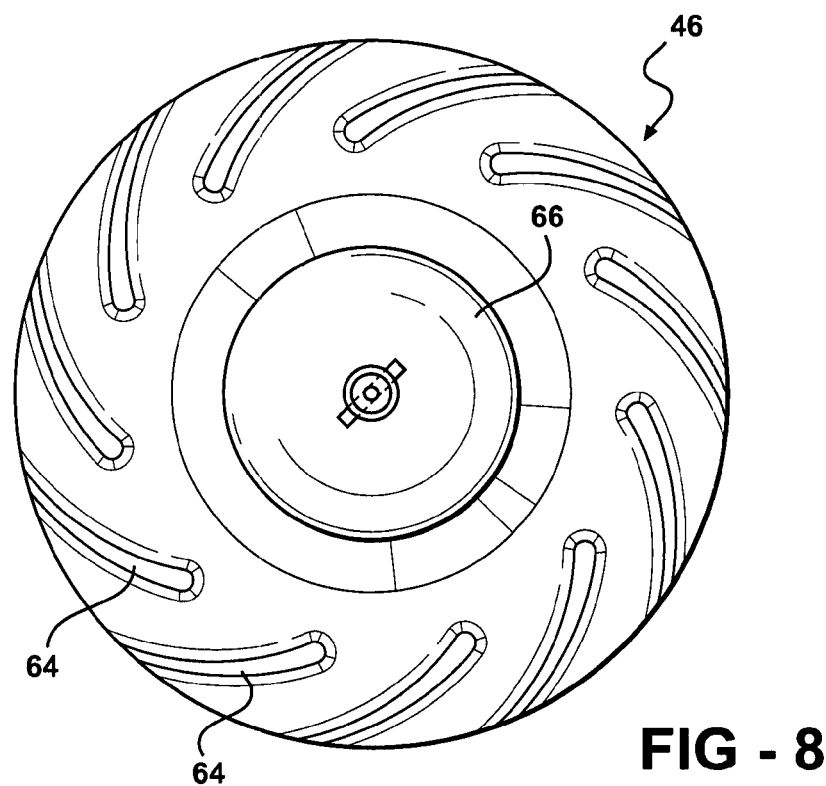
FIG. 8 is a top view of the fan showing the fan blades having air foil shapes.

Referring now to FIG. 7, the fan 46 includes a plurality of curved blades 64 and a hub portion 66. The curved blades 64 of the fan 46 encourage air into the scroll housing 50. The blades 64 are further defined as centrifugal fan blades having a foil cross-section, i.e., the blades 64 taper along their length. This configuration moves air more efficiently and more quietly than blades 64 with a constant thickness. The foil cross-section of each of the blades 64 preferably has an angle of attack of from 30 to 50 degrees. The fan 46 is preferably formed of glass-filled polypropylene, more preferably 30% glass-filled polypropylene.

Referring back to FIG. 4, the scroll housing 50 includes a base portion 68 and an outer wall 70 circumferentially extending around the base portion 68. The outer wall 70 includes an upper edge 72. The scroll housing 50 further includes at least one air inlet 74 and at least one air outlet 76. In the preferred embodiment, the scroll housing 50 includes a plurality of air outlets 76, i.e., at least two air outlets 76. Other embodiments of the present invention (not shown) may also only include the fan module 42 without the scroll housing 50. In such embodiments, the at least one air inlet 74 and the at least one air outlet 76 can be described as components of the fan module 42.

The scroll housing 50 of the preferred embodiment may include an inclined surface 78 (or cutoff) along the outer wall 70 at one or more of the air outlets 76. The inclined surface 78 in the preferred embodiment is inclined relative to a rotational axis of the fan 46 and motor 48. The inclined surface 78 moves air more efficiently through the air outlet 76. In effect, a blade-pass frequency at each air outlet 76 employing the inclined surface 78 is altered such that at least two blades 64 pass the air outlet 76 simultaneously. The outer wall 70 is preferably wrapped outwardly away from the fan 46 at the outlet with the inclined surface 78 such that a flange portion 80 of the outer wall 70 defines the inclined surface 78. Preferably, the outer wall 70 is rounded at the flange portion 80 to provide a smooth transition to the air outlet 76. This reduces noise from the air flowing through the air outlet 76.

Referring again to FIG. 2, the helmet assembly 22 further includes an intake grid 82 mounted to the outer shell portion 32. The intake grid 82 includes a top surface 84 spaced from the outer shell portion 32 of the helmet assembly 22. The intake grid 82 is contoured to the outer shell portion 32 between the front and rear of the shell 28. Air is drawn into the scroll housing 50 through the intake grid 82 by the fan 46. The blades 64 of the fan 46 are dimensioned such that a top of each of the blades 64 is from about 0.14 to 0.20 inches below the upper edge 72 of the outer wall 70 of the scroll housing 50. This provides clearance between the blades 64 and the outer shell portion 32 above, which results in low noise and high efficiency.

The air inlet 74 of the scroll housing 50 is in direct communication with a hole 86 formed within the outer shell portion 32 of the shell 28 for drawing air into the scroll housing 50. In alternative embodiments of the present invention, an external structure, not shown in the Figures, can be mounted external to the helmet assembly 22 to establish the air inlet 74 of the scroll housing 50 for drawing air into the scroll housing 50. The hole 86 formed in the outer shell portion 32 may be circular in shape. The diameter of the hole 86 may be sized in relation to a diameter of the fan 46 such that only a portion of the fan 46 diameter is exposed when viewed through the air inlet 74 in the outer shell portion 32. This ratio of air inlet 74 diameter to fan 46 diameter may be from 1:2 to 1:1, more preferably, from 1:1.5 to 1:1.1.

Referring to FIG. 4, a support pedestal 88 protrudes from the motor mount 60. Preferably, the support pedestal 88 is integrally formed as a part of the motor mount 60, which is fixed to the base portion 68. Alternatively, it is also to be understood that the support pedestal 88 can be a separate part. That is, the support pedestal 88 can be a separate part that is mounted or connected to the base portion 68 of the scroll housing 50 via connecting screws, snap-fit, and the like. The hub portion 66 of the fan 46 is rotatably mounted in the scroll housing 50 about the support pedestal 88. The motor 48 of the fan module 42 is mounted within an underside of the support pedestal 88 for space-saving purposes in the helmet assembly 22. As appreciated, the underside of the support pedestal 88 is essentially hollow. The motor 48 shaft protrudes through an opening in the support pedestal 88 to rotatably engage the fan 46. The cover plate 54 operates as a motor 48 cover to close the fan module 42 at the inner shell portion 30. The motor 48 has a pair of bearings, as will be appreciated by those skilled in the art. The fan 46 is configured with a center of gravity that is centered between the motor 48 bearings. This reduces force moments about the motor 48 bearings thus reducing stress to the motor 48 bearings. In essence, loads on the fan 46 are thus shared between the motor 48 bearings.

In operation, the motor 48 rotates the fan 46 to draw air into the air inlet 74 of the scroll housing 50 through the intake grid 82 and the air inlet 74 in the outer shell portion 32 and distributes air out of the scroll housing 50 through the air outlet 76 or outlets and into the air flow channel 34 where the air is distributed about the head 24 of the user. Cutoffs (in some embodiments, inclined cutoffs as previously described) cut the air as the fan 46 moves the air within the scroll housing 50. More specifically, as shown in the Figures, the present invention incorporates several air flow cutoffs in the scroll housing 50 to cut the air. A power supply is incorporated in the present invention to power the motor 48 to rotate the fan 46 via the motor 48 shaft. Preferably, the power supply is a rechargeable DC battery. Also preferred, the power supply is disposed within, i.e., integrated into, the helmet assembly 22. In such a case, the power supply is referred to as an integral power supply. Alternatively, the power supply can be mounted to the body 26 of the user (not shown). The power supply powers the motor 48 through pulse width modulation (PWM) which will be discussed further below. The design of the scroll housing 50 provides more efficient movement of air with less power being required from the power supply overall. Furthermore, in addition to such reduced power requirements, the scroll housing 50 provides that sufficient air flow can be maintained with overall less air velocity. This results in a quieter helmet assembly 22.

With respect to the at least two air outlets 76, the outer wall 70 of the scroll housing 50 is partitioned to define the air outlets 76. In the preferred embodiment of the present invention having the at least two air outlets 76, it is to be understood that the present invention is not limited to at least two air outlets 76. That is, the present invention may include, for example, three or four air outlets 76. The air outlets 76 provide a complete balance of air as the air is distributed from the scroll housing 50 about the head 24 of the user. To accomplish this, the helmet assembly 22 includes at least two helmet air exits 90, 92 in fluid communication with the air flow channel 34. The air outlets 76 are in fluid communication with the at least two helmet air exits 90, 92 to distribute the air from the air outlets 76, which is in the air flow channel 34, toward the head 24 of the user. In the preferred embodiment of the present invention where the helmet assembly 22 includes the at least two helmet air exits 90, 92 it is not critical that the scroll housing 50 include at least two air outlets 76. To the contrary, the scroll housing 50, in these embodiments, may only have at least one air outlet 76. Furthermore, the helmet assembly 22 may also have only one air exit.

In an alternative embodiment, at least one air bleed valve (not shown) may be incorporated in the scroll housing 50 to influence the amount, or the volume, of air flowing into the air flow channel 34 from each of the air outlets 76. This is shown in the '019 patent to Diaz et al., which is hereby incorporated by reference.

In the preferred embodiment, as best shown in FIG. 2, the air exits 90, 92 are a front air exit 90 and a rear air exit 92 in that they are disposed at a front section 94 and a rear section 96 of the helmet assembly 22, respectively, to effectively distribute air toward both the face and neck of the user. However, in alternative embodiments, the air exits 90, 92 can be disposed in alternate locations to distribute air toward any portion of the user's head 24. For instance, the air exits 90, 92 can be side air exits 90, 92 such that air is distributed toward the side of the user's head 24. For descriptive purposes only, the present invention will be described below only in terms of front and rear air exits 90, 92 and will be numbered accordingly. More specifically, the front air exits 90 are disposed at the front section 94 for distributing air from the air flow channel 34 toward the front of the head 24 of the user, and the rear air exits 92 are disposed at the rear section 96 for distributing air from the air flow channel 34 toward the back of the head 24 of the user.

Still referring to FIG. 2, the air flow channel 34 defined between the inner and outer shell portions 30, 32 terminates at the front section 94 with the front air exits 90. More specifically, the inner and outer shell portions 30, 32 converge toward the front section 94 to define the front air exits 90. The front air exits 90 may have an air deflector (not shown) defined between the outer shell portion 32 and the inner shell portion 30 wherein the outer shell portion 32 angles toward the inner shell portion 30 at the front air exits 90 for proper deflection of air toward the front of the head 24 of the user. Such an air deflector is best shown in the '019 patent to Diaz et al., hereby incorporated by reference. The air flow channel 34 diverges upon approaching the front air exits 90. The convergence and divergence of the air flow channel 34 maintains a balanced flow of air about the user's head 24. Ultimately, this also has the effect of minimizing or even completely eliminating noise within the helmet assembly 22 due to the air flow.

The rear air exits 92 are incorporated in a nozzle assembly 98 (also referred to as a duct 98 or a duct assembly 98). Referring to FIG. 9, the nozzle assembly 98 includes two conduit-defining nozzles 106. Nozzles 106 extend downwardly from a three-sided guide member 104. As seen in FIG. 2, the guide member 104 is disposed in shell so as to divert air from at least one of the air outlets 76 into the nozzles 106. Nozzles 106 may be referred to herein as conduit-defining discharge members 106, or simply discharge members 106. As seen in FIGS. 1 and 2, the nozzles 106 extend over the back of and are separate from a head band 108 that is part of the assembly that supports the housing 50 and its contents above the head of the wearer. Nozzles 106 feed air to the rotatably adjustable nozzle tips 102 and the rear air exits 92 are defined in the nozzle tips 102. As shown in FIG. 2, the nozzle tips 102 and rear air exits 92 extend below the front air exits 90 and direct air against the neck of the user, when the personal protection system is mounted to the user. As also illustrated in FIG. 2, the nozzle tips 102 and, therefore, the rear air exits 92 are located below the back of the head band 108 of the helmet assembly 22

Referring to FIG. 10, each of the tips 102 includes a head 110 defining the rear air exit 92 of the tip. Each of the tips 102 also includes a pair of snap-locking fingers 112 for rotatably locking the tip 102 to the nozzle 106. Referring to FIG. 11 along with FIG. 10, the each nozzle 106 includes a inner flange 114 disposed in the open end of the nozzle. The snap-locking fingers 112 integral with the complementary tip 102 are axially retained by the inner flange 114 once snap-locked to the nozzle 106. The tip 102 includes an outer flange 116 that abuts the distal open end of the nozzle 106 to further axially retain the tip 102. A cylindrical shoulder 118 of the outer flange 116 of the tip 102 fits inside the open end of the nozzle 106 to rotatably support the nozzle tip 102. The snap-locking fingers 112 extend from the shoulder. In addition, a plurality of detent fingers 120 extend from shoulder to ride along a plurality of corrugations 122 defined in an inwardly protruding surface of the inner flange 114. This allows the tips 102 to rotate in the nozzles 106 in a stepped and controlled manner to prevent incidental rotation of the tips 102. As seen by the arrow extending out of the nozzle of FIG. 2 (arrow not identified) since the air exits 92 are below the head band 108, air can be discharged from the tip 102 to flow below and across the head band onto the back of the neck of the wearer. The tips 102 can be adjusted to change the direction of airflow toward or away from the neck of the user, based on the user's preference. In alternative embodiments, an adjustable deflector (not shown) could be incorporated in the tips 102 to further vary the location on the back of the user's neck to which the air from the rear air exits 92 is directed.

Nozzles 106 and guide member 104 are preferably formed of ABS, while the 102 are preferably formed of LEXAN® polycarbonate. Of course, the nozzles 106 and guide member 104 and tips 102 may be formed of other suitable materials known to those skilled in the art.

Figure 12:
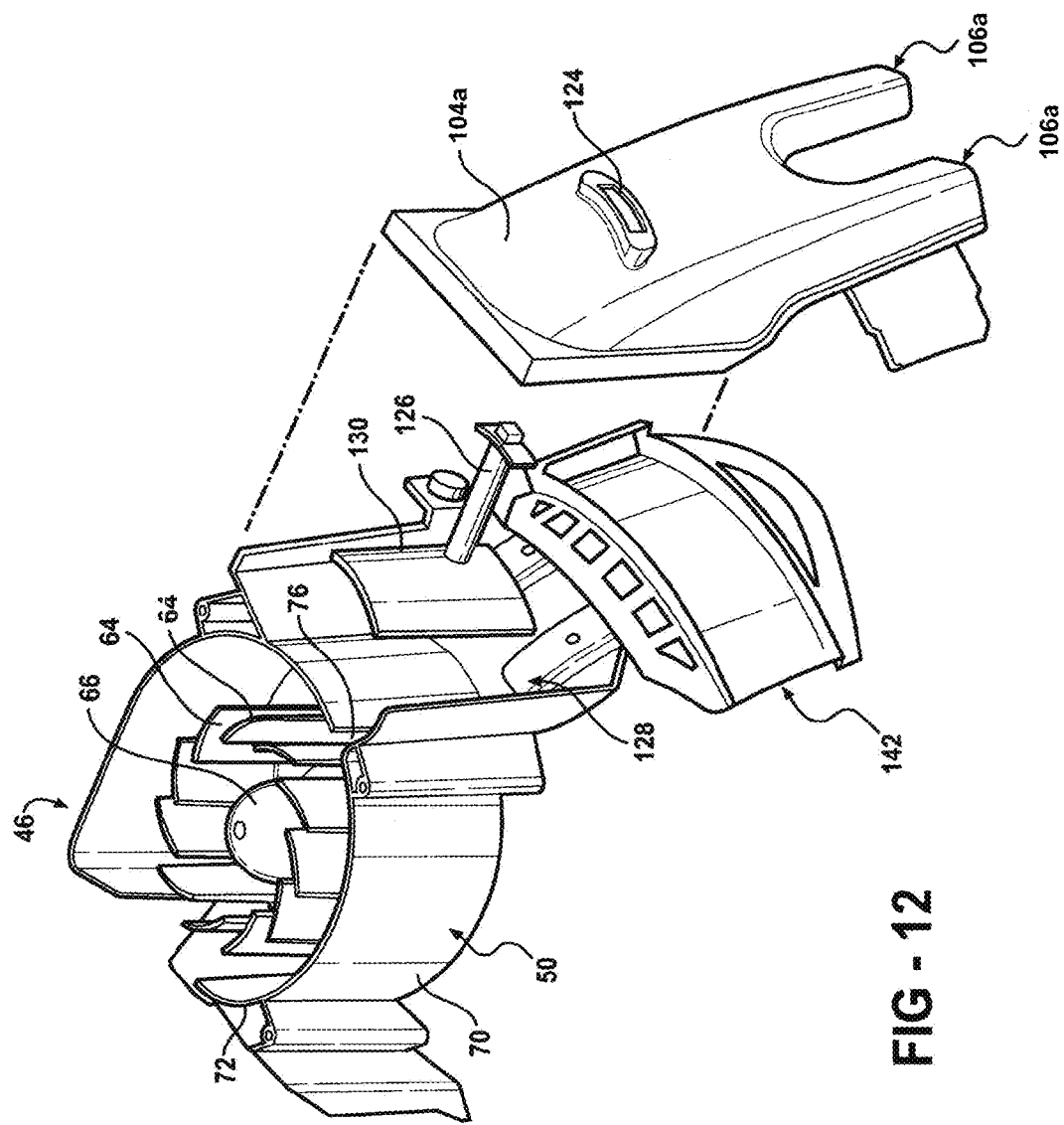
FIG. 12 is an exploded view of a first alternative nozzle of the present invention and a first adjustable air flow volume mechanism.
Figure 13:
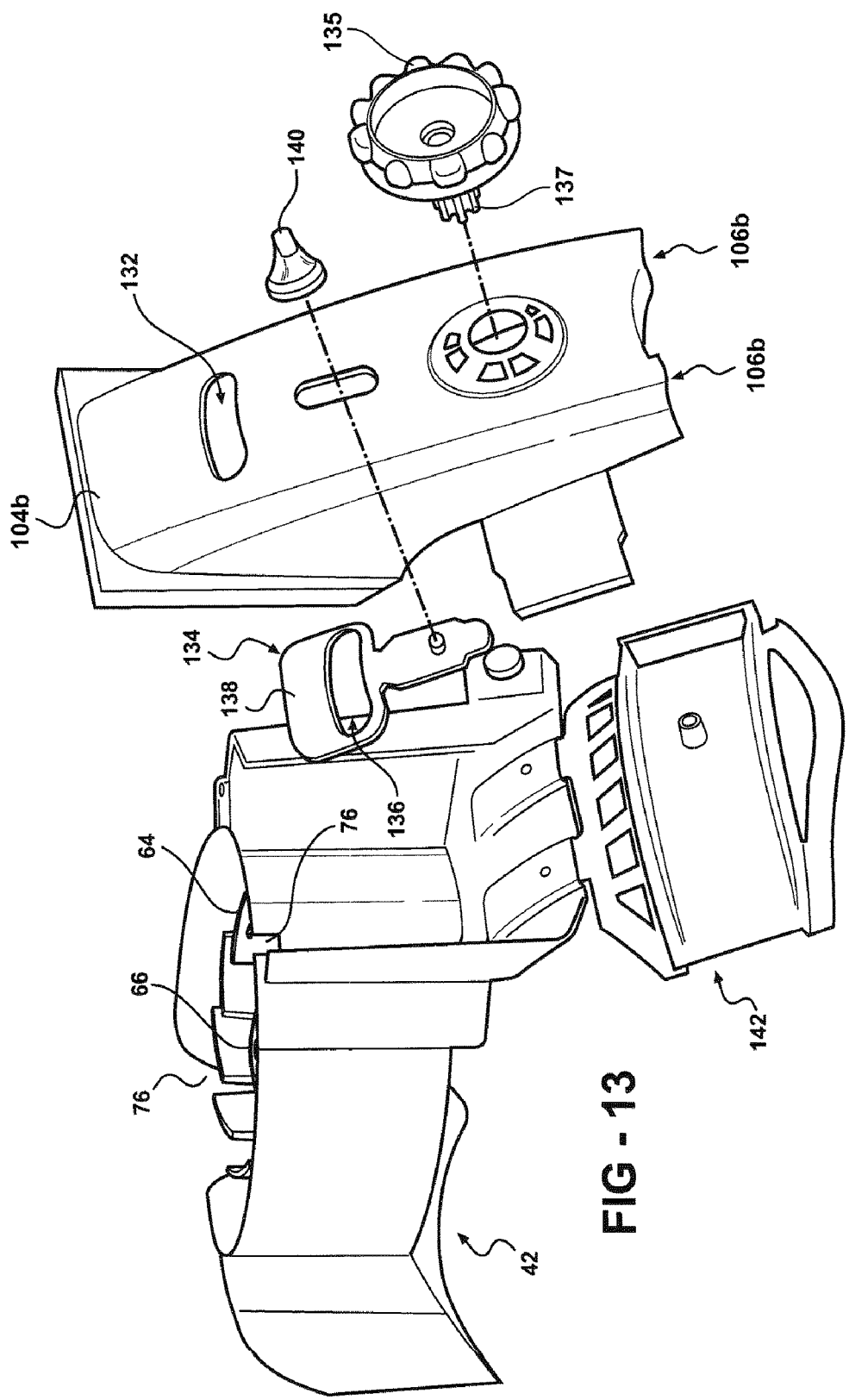
FIG. 13 is an exploded view of a second alternative nozzle of the present invention and a second adjustable air flow volume mechanism.

Referring to FIGS. 12 and 13, alternative nozzles and adjustable air flow volume mechanisms for use therewith are shown. Referring first to FIG. 12, first alternative nozzles 106a are shown as extending from a guide member 104a formed to have an aperture 124. The aperture 124 is adapted to slidably receive an arm 126 of an airflow closer 128 disposed in the air flow channel 34. A user of the helmet assembly 22 may adjust the air flow volume out through the nozzles 106a, and subsequently through the rear air exits 92 by varying the position of the airflow closer 128. By sliding the arm 126 in the aperture 124, the user can adjust a position of a baffle 130 of the air flow closer. As the baffle 130 is adjusted toward the air outlet 76 of the scroll housing 50, the air flow through the air outlet 76 to the nozzles 106a is reduced, and vice versa. The airflow closer 128 may be positioned at a fully open position, a fully closed position, or at any number of intermediate positions therebetween.

Referring to FIG. 13, the nozzles 106b extend from a guide member 104b shaped to define a nozzle vent 132. An adjustable air flow volume mechanism is in the form of a slider 134. The slider 134 is movable between a plurality of positions. In a wide open position, a slider vent 136 in the slider 134 is lined-up with the nozzle vent 132 in the guide member 104b. As a result, a large air flow volume from the air outlet 76 of the scroll housing 50 is released from the guide member 104b before reaching the nozzles 106*b*. This significantly reduces the air flow volume through the rear air exits 92. In a fully closed position, the nozzle vent 132 is closed by a panel 138 of the slider 134 and the full air flow volume from the air outlet 76 in the scroll housing 50 is directed to the rear air exits 92. A knob 140 is attached to the slider 134 through a slot in the guide member 104*b* and is used by the user to vary the position of the slider 134 and control the air flow volume.

A method of maintaining a constant volume of air flowing into the helmet assembly 22 during or throughout the entire use of the personal protection system 20 by the user is provided by the present invention. The method includes the step of selectively activating and deactivating the power supply as detailed in the '677 patent, which is hereby incorporated by reference.

Referring again to FIG. 3, head band 108 is adjustable to assist in minimizing the strain on the head 24 and the neck of the user. Strain and torque on the head 24 and neck of the user is minimized by maintaining the weight of the fan module 42 over the neck of the user even upon adjustment of the helmet assembly 22 to fit various sized heads 24. A rear support 142 extends from the back of the head band and rigidly extends to the shell 28 and is connected to the rear section 96. It is to be understood that the rear support 142 can be a separate part that is connected to the helmet assembly 22 or can be an integral part of the helmet assembly 22. In the preferred embodiment, the rear support 142 is connected to and extends from the rear section 96 of the inner shell portion 30. However, it is to be understood that the rear support 142 can connect to and extend from any portion of the shell 28. Rear support 142, it should be appreciated holds the shell above the back of the head band 108. As seen in FIGS. 2 and 13, a knob 135 with a forward extending shaft 137 is rotatably mounted to the rear support. Knob 135 and shaft 137 are part of the assembly discussed in the incorporated by reference '677 patent for adjusting the size of head band 108. In the version of the invention illustrated in FIG. 1, nozzles 106 are positioned to flow air on either side of the shaft 137. In the version of the invention illustrated in FIG. 13, the post extends through guide member 104*b*. Accordingly, within the guide member, the air discharged through nozzles 106*b* flows around the opposed sides of the shaft. A strap 175, seen in FIGS. 2 and 3, extends upwardly from the head band 108 to the bottom of the shell to further support the shell on the head 24.

Viscoelastic foam pads (not shown) may be applied to the helmet assembly 22 at various locations to provide a comfortable barrier between the user and the helmet assembly 22. In the preferred embodiment, the materials used to form the helmet assembly 22, particularly the materials used to form the shell 28, scroll housing 50, and the fan 46, were selected based on their sound-dampening characteristics. The stiffness of these materials was selected to reduce vibration and change the frequency of transmitted sound to more appeasing frequencies.

Referring back to FIG. 1, the personal protection system 20 includes a hood 144 for covering the helmet assembly 22, which houses the head 24 of the user. The hood 144 operates as a filter medium to filter air between the user and the external environment as described in the '019 patent, which is incorporated by reference.

Figure 14:
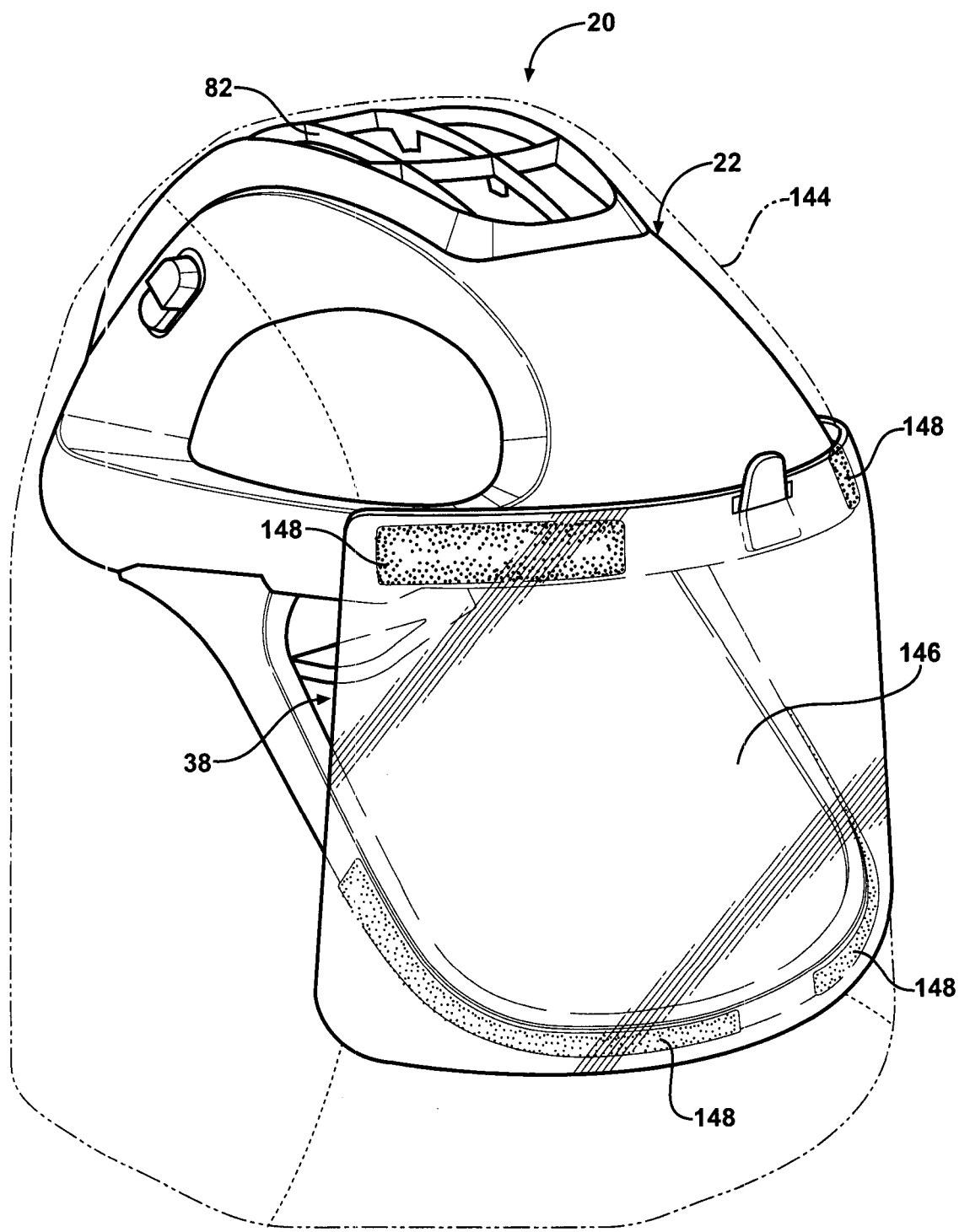
FIG. 14 is a perspective view a hood having an integrated face shield attached to the helmet assembly.

Referring now to FIG. 14, the present invention also includes a face shield 146 that permits the user to view through the hood 144 and the facial opening 38 of the helmet assembly 22. The face shield 146 may include anti-reflective and/or anti-refractive coatings to enhance vision through the face shield 146. The face shield 146 is mounted to the hood 144 such that the face shield 146 covers the facial section 36 and the facial opening 38 of the helmet assembly 22 once the user dresses into the personal protection system 20. More specifically, the face shield 146 is attached to the hood 144 to maintain a complete barrier between the user and the external environment. The facial opening 38 of the helmet assembly 22 essentially receives the face shield 146. Preferably, the facial section 36 of the helmet assembly 22 includes a hook-and-loop fastener sections 148 to further facilitate attachment of the face shield 146 to the facial section 36 for covering the facial opening 38.

Figure 15:
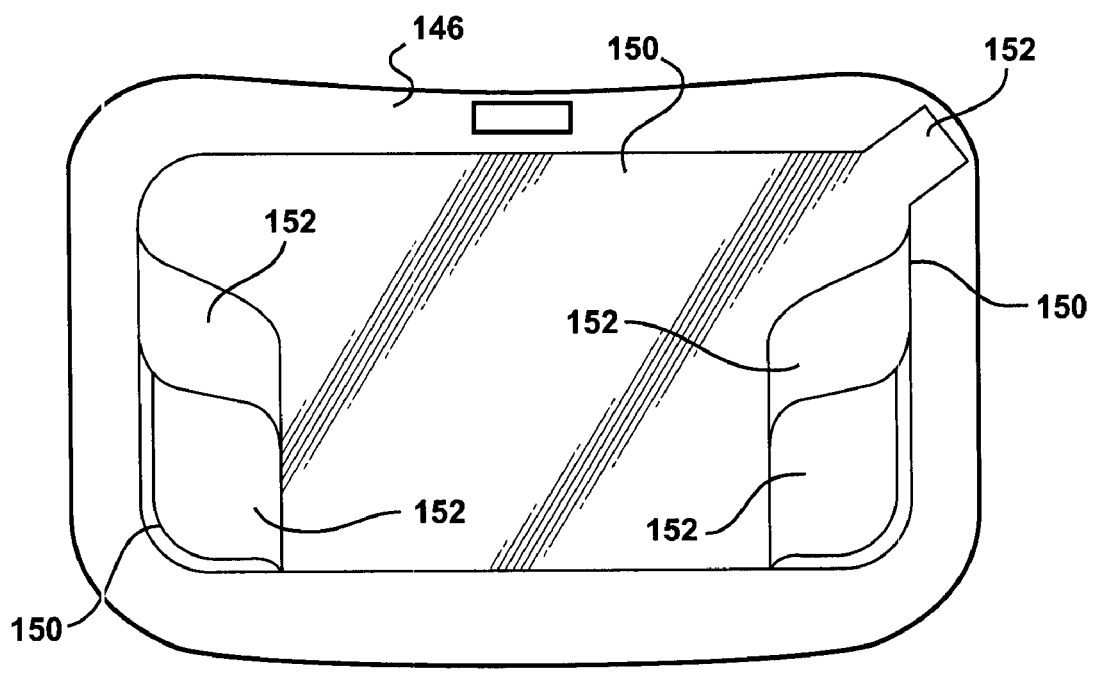
FIG. 15 is an elevational view of a removable face shield layer attached to the face shield.

Referring to FIG. 15, the face shield 146 incorporated into the hood 144 or gown preferably includes at least one removable or peelable layer 150 that provides an easier and effective manner of removing debris accumulated on the face shield 146 during use. This will eliminate the need to wipe the face shield 146 of the accumulated debris during use. In the most preferred embodiment, multiple removable layers 150 are used. These removable layers 150 would be delivered to the user in a sterile fashion with the face shield 146 being sterilized between the removable layers 150 so that no contaminates are present or exposed after removing the removable layers 150 away from the face shield 146. The removable layers 150 are transparent and preferably flexible. In one embodiment, the removable layers 150 are thin, flexible, and conform to the shape of the face shield 146. Furthermore, air gaps between the removable layers 150 are minimized to reduce multiple reflected/refracted images. Preferably, the removable layers 150 are sterilized using gamma radiation. In the preferred embodiment, the face shield 146 and removable layers 150 are assembled. The face shield 146 and removable layers 150 are then sterilized with gamma radiation. The sterilized face shields 146 with removable layers 150 are then attached to the hood 144 in a clean room environment. The hood 144 or gown with the attached face shields 146 are then individually packaged and sterilized with ethylene oxide.

However, in an alternative embodiment, the removable layers 150 may be sterilized with Ethylene Oxide (EtO) gas. In this embodiment, the removable layers 150 must be breathable for effective EtO gas sterilization.

In one embodiment, the removable layers 150 are attached directly to the face shield 146 using a self-adhering method of attachment such as static forces, transparent adhesive, and the like. As shown, the removable layers 150 may include peel tabs 152 that the user or an assistant can grab to peel-away the removable layers 150 from the face shield 146. The tabs 152 can be positioned at any portion of the removable layers 150 such as at the top for "peel down" removal, at the bottom for "peel up" removal, or at the side for "peel across" removal. Furthermore, each of the removable layers 150 may have multiple tabs 152. The removable layers 150 preferably include anti-reflective and/or anti-refractive coatings to improve vision by reducing multiple images. In one embodiment, the removable layers 150 are formed from a 1 to 5 mil clear urethane film. In further embodiments, the removable layers 150 are formed of polyester, e.g., Mylar®, or other gamma radiation stable materials to reduce or eliminate air layers 150 between adjacent removable layers 150.

In an alternative embodiment, the removable layers 150 are thin and semi-rigid or rigid and conform to the shape of the face shield 146, while still minimizing the air gap between adjacent removable layers 150. The removable layers 150 may be formed as a semi-rigid or rigid film. In this embodiment, the removable layers 150 may be attached at a periphery of the face shield 146 in a non-continuous manner such as by adhesive, tape, spot-welding, static cling attachment, or other conventional methods of attachment. This allows EtO gas to penetrate the periphery for terminal sterilization between the removable layers 150. In this embodiment, the removable layers 150 may be manufactured in a flat configuration and then wrapped to conform to the curvature of the face shield 146, which minimizes the air gaps between the removable layers 150 to reduce unwanted images when looking through the face shield 146 and the removable layers 150. The removable layers 150 in this embodiment may also include anti-reflective and/or anti-refractive coatings to improve vision and may also include tabs 152 to remove the removable layers 150.

In further embodiments, the removable layers 150, whether thin and flexible or thin and semi-rigid or rigid, may be polarized using a polarized coating. The removable layers 150 may also include magnification coatings to improve the user's view. Magnification may be carried out solely by the removable layers 150, or in alternative embodiments, magnification may be carried out by a combination of the removable layers 150 and the face shield 146. In even further embodiments, magnification is carried out solely by the face shield 146. In addition, the removable layers 150 may provide UV protection by using UV inhibiting films or adhesives.

The face shield 146 may be packaged with multiple removable layers 150 ready for removal from the face shield 146 during use. However, in some instances it may be beneficial to provide a user with greater flexibility in selecting the types of removable layers 150 to be used, e.g., thin and flexible or thin and semi-rigid or rigid, or to provide the user the option of selecting whether the removable layers 150 will be used at all. To this end, each removable layer 150 (flexible, semi-rigid, or rigid) is packaged separately from the face shield 146 incorporated into the hood 144 or gown. As a result, the user can choose, which, and how many, of the removable layers 150 to attach to the face shield 146 prior to use. Alternatively, a removable layer 150 (flexible, semi-rigid, or rigid) may be separately packaged and formed with anti-reflective, anti-refractive, and/or magnification coatings to improve image quality for the user. In this instance, the coatings may work with complementary coatings on the face shield 146 to improve the image quality for the user, or the removable layer 150 may be the sole source of these coatings.

In the event that the removable layers 150 are separately packaged, they will also be separately sterilized using either EtO gas sterilization, or preferably gamma radiation sterilization. When gamma radiation sterilization is used, the air layers 150 between adjacent removable layers 150 can be reduced or eliminated, which improves image quality through the removable layers 150. The use of gamma stable materials to form the removable layers 150 also improves optical clarity.

The present invention preferably includes a positioning and supporting system for assisting a single user in self-gowning as the user maintains sterility. This system is fully described in the '019 patent to Diaz et al., hereby incorporated by reference. The present invention may also include a visual positioning system as disclosed in the '019 patent to Diaz et al., hereby incorporated by reference.

Obviously, many modifications and variations of the present invention are possible in light of the above teachings. The invention may be practiced otherwise than as specifically described within the scope of the appended claims. In addition, the reference numerals in the claims are merely for convenience and are not to be read in any way as limiting.

What is claimed is:

1. A personal protection system for fitting over a head and a neck, said system comprising:
    a head band having a rear section that extends around a back of the head;
    at least one support member mounted to said head band;
    a shell attached to said at least one support member, wherein said at least one support member and said shell are collectively shaped so that said shell is located above the head and above said head band rear section;
    a fan mounted in said shell that draws air into said shell;
    a nozzle assembly connected to said shell for receiving air discharged by said fan, said nozzle assembly including: a conduit that receives the air discharged by said fan, said conduit extending downwardly from said shell so as to extend at least partially over said rear section of said head band; and a tip located at an end of said conduit distal to said shell, said tip having an exit located below said headband opening through which air can be discharged below said rear section of said head band onto the back of the neck;
    a hood that is disposed over said head band, said shell and said nozzle so as to extend over the head and the neck, said hood having a transparent face plate that is positioned to be forward of a front of the head; and
    a fastening assembly connected to at least one of said shell or said hood for releasably holding said hood to said shell.

2. The personal protection system of claim 1, wherein said nozzle assembly conduit is rigidly connected to said shell.

3. The personal protection system of claim 1, wherein:
    said head band has a front section that extends around the front of the head;
    at least one first support member extends upwardly from said front section of said head band to support said shell above the head; and
    at least one second support member extends upwardly from the rear section of said head band to support said shell above the head.

4. The personal protection system of claim 1, wherein said nozzle assembly is separate from said head band.

5. The personal protection system of claim 1, wherein said nozzle assembly conduit and said tip are dimensioned so that the tip exit opening is located below the rear section of said head band.

6. The personal protection system of claim 1, wherein:
    said head band has a front section that extends around the front of the head; and
    an outlet duct extends from said shell to a position forward of said front section of said head band, said outlet duct receiving air discharged by said fan and having an opening through which the air is discharged forward of said front section of said head band.

7. The personal protection system of claim 6, wherein said fastening assembly includes a fastening component attached to said outlet duct for releasably holding said hood forward of said outlet duct.

8. The personal protection system of claim 6, wherein said outlet duct is a rigid structure.

9. The personal protection system of claim 1, wherein said tip of said nozzle assembly can be rotated relative to said nozzle assembly conduit.

10. The personal protection system of claim 1, further including:
    a rotating knob with a shaft, said shaft being connected to said head band and extending outwardly from said back portion of said head band, said knob and said shaft cooperating with said head band for adjusting said head band; and wherein
    said nozzle assembly is constructed so as to flow air around opposed sides of said shaft.

11. A personal protection system for fitting over a head and a neck, said system comprising:
- a head band that extends at least partially around the head, said head band having a front portion that extends around a front of the head and a back portion that extends around a rear of the head;
- a plurality of spaced apart support members that extend upwardly from said head band;
- a shell mounted to said support members, said support members and said shell being shaped to hold said shell above the head, said shell being located above said back portion of said head band;
- a fan mounted to said shell for drawing air into said shell;
- an outlet duct that extends forward from said fan that receives air discharged from said fan, said outlet duct extending in front of said head band front portion and having an opening through which air is discharged to below said head band;
- a duct assembly located below and rearward of said shell, said duct assembly having: a duct structure that extends over said back portion of said head band that is connected to said shell for receiving air discharged from said fan; and a tip located below and in fluid communication with said duct structure, said tip having an exit opening located below said head band through which air can be discharged therefrom across a bottom edge of said back portion of said head band towards the back of the neck;
- a hood removably disposed over said head band, said shell, said outlet duct and said duct assembly, said hood having a transparent face shield located forward of said head band front portion; and
- a fastening assembly connected to at least one of said shell or said hood for releasably holding said hood to said shell.

12. The personal protection system of claim 11, wherein said duct structure is rigidly connected to said shell.

13. The personal protection system of claim 11, wherein said duct structure and said tip are collectively shaped so that said tip exit opening is located below said head band back portion.

14. The personal protection system of claim 11, further including:
- a rotating knob with a shaft, said shaft being connected to said head band and extending outwardly from said back portion of said head band, said knob and said shaft cooperating with said head band for adjusting said head band; and wherein
- said duct structure is constructed so as to flow air around opposed sides of said shaft.

15. A personal protection system for fitting over a head and a neck, said system comprising:
- a head band that extends at least partially around the head, said head band having a back portion that extends around a rear of the head;
- at least one support member that extends upwardly from said head band;
- a shell mounted to said at least one support member, said support member and said shell being shaped to hold said shell on the head, said shell being located above said back portion of said head band;
- a fan mounted to said shell for drawing air into said shell;
- a duct assembly located below and rearward of said shell, said duct assembly having: a duct structure that extends over said back portion of said head band that is connected to said shell for receiving air discharged from said fan; and a tip located below and in fluid communication with said duct structure, said tip having an exit opening located below said back portion of said head band through which air can be discharged therefrom across said back portion of said head band and towards a back of the neck;
- a hood removably disposed over said head band, said shell and said duct assembly, said hood having a transparent face shield located forward of a front portion of said head band; and
- a fastening assembly connected to at least one of said shell or said hood for releasably holding said hood to said shell.

16. The personal protection system of claim 15, further including an outlet duct that extends forward from said fan that receives air discharged from said fan, said outlet duct extending in front of said head band front portion and having an opening through which air is discharged to below said head band.

17. The personal protection system of claim 15, wherein said duct structure is rigidly connected to said shell.

18. The personal protection system of claim 15, wherein:
- said duct structure includes a plurality of nozzles; and
- said duct assembly includes a plurality of tips, each said tip being attached to a separate one of said duct structure nozzles.

19. The personal protection system of claim 15, further including:
- a rotating knob with a shaft, said shaft being connected to said head band and extending outwardly from said back portion of said head band, said knob and said shaft cooperating with said head band for adjusting said head band; and wherein
- said duct structure is constructed so as flow air around opposed sides of said shaft.

20. The personal protection system of claim 15, wherein said duct structure is separate from said head band.

* * * * *

UNITED STATES PATENT AND TRADEMARK OFFICE
CERTIFICATE OF CORRECTION

PATENT NO. : 7,752,682 B2
APPLICATION NO. : 11/277424
DATED : July 13, 2010
INVENTOR(S) : Brian J. VanDerWoude et al.

Page 1 of 1

It is certified that error appears in the above-identified patent and that said Letters Patent is hereby corrected as shown below:

IN THE CLAIMS:

In Column 12, line 13, Claim 1, insert --opening-- between 'exit' and 'located'.

In Column 12, line 14, Claim 1, delete "opening".

Signed and Sealed this

Thirty-first Day of August, 2010

David J. Kappos
*Director of the United States Patent and Trademark Office*